United States Patent [19]

Arntz et al.

[11] 4,442,308

[45] Apr. 10, 1984

[54] PROCESS FOR PREPARING BY CATALYTIC OXIDATION IN OXYGEN-CONTAINING GAS MIXTURES, ACROLEIN FROM PROPYLENE AND METHACROLEIN FROM ISOBUTYLENE OR TERTIARY BUTANOL

[75] Inventors: Dietrich Arntz; Günter Prescher, both of Hanau; Johannes Heilos, Seligenstadt, all of Fed. Rep. of Germany

[73] Assignee: Degussa Aktiengesellschaft, Frankfurt am Main, Fed. Rep. of Germany

[21] Appl. No.: 390,448

[22] Filed: Jun. 21, 1982

[30] Foreign Application Priority Data

Jun. 26, 1981 [DE] Fed. Rep. of Germany ....... 3125061

[51] Int. Cl.$^3$ ........................ C07C 45/35; C07C 45/38
[52] U.S. Cl. ..................................... 568/480; 568/479; 502/212
[58] Field of Search ............... 568/479, 480, 477, 471, 568/470; 252/435, 437

[56] References Cited

U.S. PATENT DOCUMENTS

| | | | |
|---|---|---|---|
| 3,454,630 | 7/1969 | Yamaguchi et al. | 568/480 |
| 3,639,269 | 2/1972 | Koberstein | 252/437 |
| 3,761,424 | 9/1973 | Koberstein | 252/437 |

FOREIGN PATENT DOCUMENTS

| | | | |
|---|---|---|---|
| 15569 | 3/1979 | European Pat. Off. | 568/479 |
| 2049583 | 2/1976 | Fed. Rep. of Germany | 252/437 |
| 2611249 | 11/1976 | Fed. Rep. of Germany | 568/479 |

*Primary Examiner*—Werren B. Lone
*Attorney, Agent, or Firm*—Beveridge, DeGrandi & Kline

[57] ABSTRACT

A process is disclosed for preparing acrolein from propylene and methacrolein from isobutylene or tertiary butanol, by oxidation in oxygen-containing gas mixtures on specially prepared coated catalysts comprised of an inert support and a coating, enclosing this support, of an oxidic catalyst material containing the elements nickel, cobalt, iron, bismuth, phosphorus, molybdenum and tantalum or samarium and, if appropriate, also alkali metal or alkaline earth metal in certain atomic ratios. This coated catalyst is obtained by spraying a suspension of the starting material for the coating, which suspension contains a binder and, if appropriate, a poreformer, from above in an increasing amount onto a bed of the support, which bed is mechanically agitated and loosened up by a gas stream blow in from below, the ratio between suspending medium sprayed on and removed again by the gas stream remaining approximately constant. The thermal expansion coefficient of the precursor as a dry powder must not deviate by more than 15% from the coefficient of the support. The coating is densified by further agitation, and the material is dried in the continuing gas stream and heat-treated, if appropriate after decomposition of an added poreformer.

21 Claims, No Drawings

PROCESS FOR PREPARING BY CATALYTIC OXIDATION IN OXYGEN-CONTAINING GAS MIXTURES, ACROLEIN FROM PROPYLENE AND METHACROLEIN FROM ISOBUTYLENE OR TERTIARY BUTANOL

The invention relates to a process for preparing acrolein from propylene and methacrolein from isobutylene or tertiary butanol, by oxidation in oxygen-containing gas mixtures on coated catalysts which contain active phases known in themselves but which have improved catalytic and mechanical properties due to preparation by a new process.

It is known that acrolein can be obtained from propylene and methacrolein can be obtained from isobutene or tertiary butanol. For this purpose, catalysts in accordance with German Patent No. 2,049,583, which contain oxides of nickel, cobalt, iron, bismuth, phosphorus, molybdenum and of rare earths together with additions of inorganic support substances, can be used. The disclosures of U.S. Pat. Nos. 3,639,269 and 3,761,424 which correspond to German Patent No. 2,049,583 are relied on in this respect.

These catalysts are customarily used in a pelletized or extruded form. When such catalysts are used in industry it is usually necessary to dilute them by inert materials in the bed.

However, these measures create problems in respect of the homogeneity of the bed and the conducting of the heats of reaction from the internal regions of the bed to the cooling medium, the result being losses in selectivity, and hence, yield.

It has been known since 1963 that these problems can be contended with by means of so-called coated catalysts, where the active catalyst phase is coated on an inert support. The temperature-equalizing effect of the support mass avoids local superheating phenomena. The diffusion paths for the gaseous reactants are short in the relatively thin coatings of active catalyst material, and catalyst activity can be adjusted to any level desired by varying the layer thickness of the active material (Austrian Patent No. 226,672 and corresponding U.S. Pat. No. 3,232,977 are relied on herein).

German Offenlegungsschrift No. 2,611,249 deals with the use of such a coated catalyst for the oxidation of propylene to acrolein. However, the process described there permits only the preparation of coated catalysts having a relatively low content of active phase, so that such a catalyst must usually be followed by a downstream unsupported catalyst, which consists through and through of active material, in order to obtain economically satisfactory conversions. However, the superposition of catalysts of differing activity is always problematical because of the necessity of matching single activities.

The known catalysts described above particularly have the disadvantage that it is necessary to dilute the synthesis gas with considerable amounts of steam. However, it is precisely the steam content in the synthesis gas which must be reduced to obtain economical reaction conditions, something that was not possible to a satisfactory degree in the case of the known industrial catalysts (Shokubai, Volume 19, 157-67 (1977) Catalyst).

European Laid-Open Application No. 0,015,569 describes a process for preparing acrolein and methacrolein by oxidation of propylene and isobutylene, respectively, in oxygen-containing gas mixtures using a coated catalyst even for low steam contents of the synthesis gas. The catalysts proposed for this purpose are prepared by applying an aqueous suspension of the catalytically active material to agitated support particles, the suspension being sprayed at a certain constant rate onto the support while the suspending medium is partially removed by means of a gas stream of 20°–300° C. and an essentially constant residual moisture of the coating being maintained.

This catalyst and other catalysts obtainable by known processes have the common disadvantage that in the case of thicker coatings, that is coatings the amount by weight of which, relative to the catalyst, exceeds 20%, the abrasion resistance and impact strength of the coating are not fully satisfactory for use in large scale industrial fixed bed reactors.

In particular, a tendency for the coating to spall under the influence of temperature gradients was found in the case of coated catalysts manufactured by means of conventional coating pans or rotary disks, which only permit the passage of a drying gas stream across the agitated material.

Moreover, only a relatively wide particle size distribution, which is determined by the particular thickness of the coating of the individual particles of the catalyst, can be obtained by means of these devices.

However, a wide particle size distribution results in, on the one hand, a markedly higher pressure drop of catalyst beds and, on the other hand, the occurrence of strongly differing heats of reaction on the individual catalyst particles, which, in total, leads to deterioration of selectivity.

The preparation process dealt with in European Laid-Open Application No. 0,015,569 requires the maintenance of a metering rate for suspension and drying gas which remains constant with time, in order to maintain the water content of the resulting coating during the spraying-on of the suspension at a virtually constant value. However, it is precisely this measure which, with increasing duration of the preparation operation, causes the outer surface of the coating to contain increasingly less liquid, which impairs or prevents the application of thicker coatings having sufficient mechanical strength. U.S. Pat. No. 4,305,843 which corresponds to the above European application is relied on herein.

Moreover, by guiding the dry gas stream over the surface of the support bed, a measure proposed there, only a moderate drying rate is obtained during the formation of the coating. The result of this is the unfavorable wide particle size distribution already mentioned.

The object of the invention is to provide a process for preparing acrolein from propylene and methacrolein from isobutylene or tertiary butanol, by oxidation in oxygen-containing gas mixtures on abrasion-resistant coated catalysts comprised of an inert support which has a particle size of 0.5 to 6 mm and a rough surface and a coating, enclosing the support and anchored in it, of active catalyst material of the composition:

$$Ni_aCo_bFe_cBi_dP_eMo_fO_x$$

in which a is a number from 2–20, b is a number from 0–15, a and b are a number from 2–20, c is a number from 0.1–7, d is a number from 0.1–4, c is a number from 0.1–4, e is a number from 0.1–4, f is about 12 and x is a number from 35–85, and 0.2 to 5% by weight of tantalum or samarium, and if appropriate, also 0.05 to 3.0% by weight of an alkali metal or alkaline earth metal, calculated as oxide, on a support substance composed of a layer lattice silicate and/or highly dispersed silica—in the first case (that is when the silicate plus silica are used) in a weight ratio of 10:1 to 1:1—which coating is obtained by spraying a suspension of the starting material for the coating onto an agitated bed of the support while the suspending medium is partially removed by a gas stream of 20°–250° C. and an essentially constant residual moisture of the coating is being maintained, and drying and heat-treating.

This object is achieved according to the invention by using coated catalysts in the preparation of which the support bed is set into mixing motion by mechanical agitation and is simultaneously loosened by blowing in from below a fluidizing, mixing-intensifying gas stream, a suspension of a precursor of the catalytically active material, which suspension contains a binder and, if appropriate, a pore-former, is passed counter-current to the gas to this bed at a rate which increases with increasing thickness of the coating, the amounts of suspending medium drawn off and sprayed on being maintained in a substantially constant ratio which is determined by the particular combination of support and precursor used and the thermal expansion coefficients of support and of dried pulverulent precursor being so chosen that they differ by at most 15%, and wherein after the spraying-on has been completed the coating is densified by continuing the increased mixing motion, the mechanical mixing motion is then stopped, the material is dried in a continuing gas stream and finally heat-treated, if appropriate after decomposition of an added pore-former.

A pore former may be added to enhance transport of reacting molecules within the catalytic system. It may be a polymer or a monomer and should be only slightly soluble in the suspending medium. The pore former must be capable of being burned off during the tempering step.

This coating process for support bodies thus proposes loosening up a support bed set in mixing motion by blowing in a gas stream from below, the gas stream passing through the fluidized charge effecting partial removal of the suspending medium. For carrying out this step, appropriately equipped mixing units are possible, such as, for example, special coating drums, coating pans or rotary disks. Those units are preferable in which drying air flows evenly through the entire bed.

In a prefereable embodiment of the process according to the invention, the coating of the coated catalyst used is applied and dried in a device in accordance with German Offenlegungsschrift No. 2,805,801, the entire disclosure of which is relied on.

In the so-called Driacoater operating in counter-current, spray liquid and dry air flow in opposite directions. This piece of equipment has been described, inter alia, in the Offenlegungsschrift mentioned above, and primarily comprises a cylindrically or conically shaped and horizontally mounted drum. Dry air is introduced exclusively from below the underside of the bed of material via air ducts located in the outer jacket of the drum through hollow ribs arranged on the inside of the drum and which are perforated on the side facing away from the direction of rotation.

When the drum revolves, the bulge-shaped hollow ribs and the drying air blown in through them effect the fluidization and thorough circulation of the bed material; that the drying air flows evenly through the latter manifests itself in a uniformly and calmly downflowing intrinsic motion of the material. Moisture-rich exit air is drawn off above the bed via the hollow uptake mandrel in the axis of rotation of the drum.

For spraying the powder suspensions used in the process according to the invention, two-material nozzles are preferably used, by means of which, more simply then in the case of one-material nozzles, the desired feed rate, with any state of fine division, can be conveniently controlled. The atomization is usually effected by means of compressed air of 0.5–2 bar, as a function of the necessary suspension throughput (which results from the size of charge, the desired thickness of the powder application and the time for preparation) by means of one or more nozzles of 2–4 mm diameter for pressures of the suspension in front of the nozzle of 1–3 bar.

For Driacoater units having charge capacities of 10–200 liters, it has proved advantageous to adjust the fluidizing gas stream to a specific flow rate of 15–50 $Nm^3$ per hour per liter of support and to heat it to 60°–100° C. Lower inlet air flow rates lead to markedly lower drying rates, less even flow through the entire bed due to wall effects along the drum walls and hence considerably longer preparation times. In contrast, inlet air flow rates which are too high cause too severe drying of the suspension on the way from the nozzle to the bed surface, which causes the resulting dried precursor powder to be carried away with the exit air and inadequate moisture of the coating during application. It hs been found that maintaining a constant moisture level of the resulting coating during the entire coating build-up is an essential prerequisite for obtaining a firmly adhering coating of active catalyst material firmly anchored in the support material. If the coating of the blanks during this coating build-up becomes too moist, several particles agglomerate with one another. However, if application is too dry, the desired anchoring in the support and also good strength of the coating cannot be obtained. It is also an essential insight that by maintaining drying inlet air which is constant in respect of temperature and rate, the necessary constant moisture of the coating can be readily controlled by the amount of suspension sprayed on per unit time. To assign nominal values for such a control, the temperature above the bed or the moisture of the exit air can be used, both of which permitting sensitive monitoring of the drying process. The most favorable nominal values themselves depend on the type of powder and on the temperature, the moisture and the amount of inlet air per unit volume of support material. Depending on the solids content of the suspension and the type of precursor, 10–50% of the sprayed-on suspending medium should remain in the coating during its build-up. It has been found that considerable improvement of the mechanical stability of the coating is obtained if not a constant nominal value but a decreasing temperature or an increasing exit air moisture are given. This makes possible, by corresponding program control, a fully automatic application of the precursor powder.

The fluidizing gas may be air, nitrogen or other inert gases. Drying of the gas is not necessary, but if the gas is not dry, it should have nearly constant humidity.

Water is preferably used as the suspending medium for the catalyst precursor present in powder form. Other liquids, such as, for example, alcohols, are not excluded and have advantages over water in various respects: they may require less vaporization energy or permit better matching of the wetting and solubility behavior of the precursor of the catalytic material and the support substance. The latter can be influenced in the case of aqueous suspensions only by adding binders. However, the advantage of organic solvents is contrasted with the disadvantage of forming ignitable mixtures with the drying air and requiring special exit air cleaning units. The suspending medium should be inert, i.e. non-reactive during the course of the process.

The solids content of the suspension is best so adjusted that the suspension comprises 20-80, preferably 40-70% by weight of pulverulent precursor. Solids contents which are too high can cause blockages in the feed and spray system for the suspension. Solids contents which are too low, however, require unnecessarily prolonged preparation times. The empirically determinable solids content which is most favorable in a particular case depends on the properties of the precursor used and its interaction with the suspending medium and is, for example, in the case of the catalysts prepared within the scope of the examples for the propene oxidation, 55%.

It has also been found that it is possible to obtain a marked improvement in the abrasion resistance of supported catalysts by the use of binders as known from granulation. Their content in the suspension depends on the type of binder and is as a rule between 0.5 and 10%. While the lower limit is fluid and the minimum amount necessary to ensure improvement of the abrasion resistance, in the case of binder concentrations which are too high the drying rate during the preparation of the coating is frequently reduced. For the precursors of the active catalyst component which were used, the best results were obtained with 2-5%, in particular about 4%, by weight of glucose or urea.

Other binders include starch, sugar, mannite, sorbite, gum arabicum, propylene glycol, stearic acid, oleic acid and glyerol. The function of the binder is to tackify the surface of the carrier and the surface of the precursor.

In the oxidation of propene to acrolein and of isobutylene or tert.-butanol to methacrolein, a retardation of the reaction due to pore duffusion is frequently observed in particular when using coated catalysts having a high proportion of active phase, that is, thick coatings. It has now been found that the addition of finely divided pore-formers sparingly soluble in the suspending medium, such as pentaerythritol, polymethyl methacrylate, polystyrene, polyvinyl alcohols or the like, can reduce this retarding influence on the reaction by the formation of macropores. The preferable content in the suspension of pore-former is 1-10% by weight. It is a prerequisite for the action of the pore-former that it can be removed again below the heat-treatment temperature by thermolysis or oxidation from the built-up coating.

It is explicitly proposed for the coated catalyst to be used in the process according to the invention, to use, for the build-up of the coating, a precursor of the catalytically active material. The term "precursor" is to be understood as meaning that the precursor material already contains all the ingredients required for producing the complete catalytically active material be a subsequent specific heat treatment.

The precursor is a preformed catalytic material in powder form which may be a dried coprecipitate or a coprecipitate which has been heat-treated below the temperature of the final tempering step. As shown in the examples which follow below, the precurosr may be oxidic or hydroxidic and is made from salt solutions.

Preferably, a coprecipitate from combined salt solutions of catalytically active elements, which coprecipitate is dried or has been calcined below the heat-treatment temperature, is used as the precursor of the catalytically active material.

The composition of this coprecipitate and its particular preparation is not specific to the process according to the invention, but depends on the desired catalytic action in the reaction when the coated catalyst is used. Usually, the precursor can be prepared analogously to known unsupported catalysts. To obtain good suspendability of the precursor in the suspending medium and a trouble-free feed of the suspension, a particle size distribution of 1-150 $\mu$m having a maximum preferably within the range of 1.5-30 $\mu$m has proved advantageous.

The process makes possible the preparation of catalysts in which the amount of pulverulent precursor is 0.1-2 times the weight of the support, this range not resulting from specific limits of the preparation process but rather from practical considerations concerning the use of the catalysts according to the invention indicated for obtaining the coated catalyst. This means that in principle even those compositions can be prepared by the process according to the invention which are outside the range indicated.

The invention also explicitly proposes that the thermal expansion coefficients of support and precursor are to be so adjusted that they substantially agree and differ at most by not more than 15%. For if these coefficients differ by more, the coating will crack in the subsequent heat-treatment step.

These cracks can become so large that flaky spalling of the coating takes place. In any case, the occurrence of cracks is associated with a sharp reduction of the mechanical stability of the coating, that is the abrasion resistance.

It has been found that matching of the thermal expansion coefficients by selecting a suitable support is only possible in some cases and is seldom adequate, since possible inert supports are all within the relatively narrow range from $50-90\times10^{-7}/°C$. (for one-dimensional expansion).

It has now been found, surprisingly, that the thermal expansion coefficient of the precursor powder can be matched to the coefficient of the support by a heat pretreatment at 250°-600° C. The particular precise conditions depend on the composition of the precursor and on the support to be used. Care must be taken here that this matching is to be carried out not for a certain temperature but for the entire temperature range of the subsequent heat treatment (the tensions between coating and support which occur in this heat treatment are responsible for possible crack formation). This means that an exact matching, which would presuppose a firmly defined reference temperature, it not possible. This is particularly due to the fact that, in the materials to be used according to the invention, different temperature dependences of the expansion coefficients are usually given for precursor and support.

In the process according to the invention, the precursor for a coated catalyst for prepring acrolein or methacrolein from propylene,, isobutylene or tertiary butanol used is an oxidic powder of the composition $Ni_aCo_bFe_cBi_dP_eMo_fO_x$ in which a is a number from 2-20, b is a number from 0-15, a and b are a number from 2-20, c is a number from 0.1–7, d is a number from 0.1–4, e is a number from 0.1–4, f is about 12 and x is a number from 35–85, and 0.2 to 5% by weight of tantalum or samarium, calculated as $Ta_2O_5$ or $Sm_2O_3$, and, if appropriate, also 0.05–3.0% by weight of an alkali metal or alkaline earth metal, calculated as oxide, on a support substance composed of, as desired, a layer lattice silicate and/or highly dispersed silica—in the first case (layer lattice silicate plus high dispersed silica) in a weight ratio of 10:1 to 1:1—are additionally used, and the coated catalyst is heat-treated for 0.05–5 hours at 520°–650° C. When an alkali metal or alkaline earth metal is used, the elements K, Na and Mg are preferable. Modification of these catalysts by alkali metals and alkaline earth metals is known in the art.

Layer lattice silicate is a silicate with a leaf structure and is easily cleaved along the crystal lattic network. Examples of such substances are montmorillonite, talc, and kaolinite. Highly dispersed silicas are made by flame hydrolysis of halosilianes, such as $SiCl_4$. These are sometimes called pyrogenic silica. Examples are Aerosil and Cab-O-Sil.

Advantageous support materials for the coated catalysts to be used within the scope of the invention have proven to be, in particular, α-alumina, aluminum silicate, magnesium silicate or silicon carbide. These are inert under the conditions of the reactions described herein. As regards the shape of the support, the process has no special demands, but spherical supports are preferable.

Nonporous or slightly porous magnesium silicate or silicon carbide is used above all when it is intended to apply the active phase only to the surface of the support and not to introduce the phase into the cavities of the support. In contrast, the catalytic material is more strongly protected and better anchored in the cavities of macroporous α-aluminas and alumosilicates and, in coatings which are not too thick (less than 20% by weight of active phase), requires a coating which is not so hard. The macropores of aluminum silicates and α-alumina should be within the range of 2–2,000, preferably 20–300, μm (90% value), in order, on the one hand, to ensure adequate strength of the support but, on the other hand, to permit the depositing of active phase in the pores.

From the point of view of a favorable behavior during coating build-up slightly porous or nonporous supports have advantages, since, in the case of these materials, a lower liquid loading of the support takes place at the start of the preparation and the moisture leaving the pores at the end of the preparation in the drying process is more difficult to control in the case of macroporous supports.

The invention also proposes that the support material should have a rough external surface because this increases the bond strength of the coating by in-depth anchoring of the catalytically active material in the support and permits uniform application to the entire support surface. In the case of smooth support material surfaces, a flaky, irregular, thick application is usually observed. It has been found to be particularly advantageous if the support surface has a roughness, characterized by the middle roughness value according to DIN 4,768/1, measured by means of the Hommel roughness meter of 5–50 μm.

The process according to the invention can be carried out particularly advantageously with the use of the new coated catalysts described in some detail above, if the oxygen-containing gas mixture supplied to the oxidation reaction has a molar ratio of olefin or alcohol to oxygen and diluting, substantially inert constituents of 1:1.5–2.5:7–20.

The oxygen-containing gas mixture can obtain as diluting, substantially inert constituents nitrogen, steam, carbon oxides and saturated aliphatic hydrocarbons having 1–5 C atoms or mixtures thereof.

In a mode of operation which, within the scope of the invention, is particularly important because it is yield-improving, the oxidation of propylene to acrolein is operated at a molar ratio of propylene:oxygen:nitrogen:steam of 1:1.5–1.8:5.5–7:2–4 and at a specific loading of 2–6 moles of propylene per kg of coated catalyst per hour.

As an alternative to this, in a possible likewise very advantageous way of operating, the oxidation of propylene to acrolein is carried out by partially or completely replacing a steam feed by an inert gas mixture (originating in the reaction or externally supplied) at a molar ratio of propylene:air:inert gas:water of 1:7–9:3–8:0–2 and at a specific loading of 2–6 moles of propylene per kg of coated catalyst per hour.

If, in this procedure,, exit gas from the reaction is used as inert gas, the exit gas is freed, before return into the reactor, from acrolein, acrylic acid and other constituents condensable within the temperature range of 0°–40° C. It is advantageous if the inert gas contains a steam content of 0.5–7% by volume.

In contrast, the oxidation of isobutene or tertiary butanol to methacrolein is best carried out at a molar ratio of isobutene or tertiary butanol:oxygen:inert gas:steam of 1:1.5–2.5:5.5–10:2–10 and at a specific loading of 1–6 moles of starting compound per kg of coated catalyst per hour.

The invention is illustrated below in more detail by means of illustrative embodiments:

EXAMPLE 1

The coprecipitate for the preparation of the active catalyst phase was prepared in the manner known from German Patent No. 2,049,583, by successively adding with stirring a solution of 0.3 kg of samarium oxide $Sm_2O_3$ in 3.5 kg of 38% strength nitric acid, 5.8 kg of pyrogenic silica (Aerosil 200 ®), 10.8 kg of montmorillonite, a solution of 23.4 kg of ammonium molybdate $(NH_4)_6Mo_7O_{24}.4H_2O$ in 31.4 kg of 3.5% strength phosphoric acid and a solution of 5.4 kg of bismuth nitrate $Bi(NO_3)_3.5H_2O$ in 4.5 kg of 7.7% strength nitric acid to a solution of 32.3 kg of nickel nitrate $Ni(NO_3)_2.6H_2O$, 1 kg of cobalt nitrate $Co(NO_3)_2.6H_2O$ and 4.5 kg of ferric nitrate $Fe(NO_3)_3.9H_2O$ in 38 kg of water. The resulting suspension of the coprecipitate was dried on a drum dryer, calcined at 530° C. in a revolving tube and then milled. The resulting powder of the precursor of the catalytically active material had a particle size distribution of 2–40 μm (>90%, maximum at 15 μm) and, at 400° C., a thermal expansion coefficient of $81 \times 10^{-7}/°C$.

By suspending 6.5 kg of this precursor powder in 4.7 kg of water with the addition of 0.5 kg of D-glucose as binder and 0.3 kg of pentaerythritol (type R, Degussa) as pore-former, the suspension for the starting material of the coating was prepared. The supports chosen for this precursor material were fired steatite spheres which have a diameter of 4 mm, are virtually nonporous and have a rough surface (middle roughness value 25 μm according to DIN 4,768/1) and the longitudinal thermal expansion coefficient of which at 400° C. is $90 \times 10^{-7}$/°C.

6 kg of this support were introduced into a Driacoater 500 and given a vigorous mixing and flowing motion in this unit by blowing in 2 m³ of preheated air at 80° C. per minute and revolving the drum at 20 rpm. 0.4 liter of the suspension was then sprayed in 2 minutes by means of a two-material nozzle onto the support thus agitated. The spraying-on of the remaining suspension was controlled via the exit air temperature from the pan in such a manner that all the time a constant moisture of the coating was observed. In this stage, the exit air temperature fell from initially 48° C. to 39° C. at the end of the application of the suspension (after 60 minutes), and the rate at which the suspension was applied increased from 0.096 to 0.104 liter per minute.

At the end of the spraying-on process, there followed, while the drum continued to revolve, a densification phase of 5 minutes and then a 20 minute drying phase at a single pan revolution per minute.

After air drying overnight, the pore-former was decomposed in the revolving tube at 400° C. and a mean residence time of 15 minutes. The catalyst was activated at 550° C. and 15 minutes residence time, likewise in the revolving tube.

The coated catalyst obtained had a hard, crack-free coating. The mean diameter of the coated catalyst obtained was 5.25 mm with a standard deviation of 0.3 mm. Abrasion was determined as amount of abraded material smaller than 2 mm after 7 minutes in a La-Roche Friabilator by rolling and falling wear at 20 rpm and it was for the heat-treated coated catalyst less than 0.2% by weight. After a heat treatment of 100 cycles of heating-up and cooling-down, in which the catalyst was heated, in each case in 0.5 hour, from 250° C. to 400° C. and then cooled down again to 250° C., the value had not significantly increased and was 0.2% by weight.

In a falling test, free fall of 100 ml of catalyst onto a hard surface through a 3.4 m long tube having an internal diameter of 20 mm, the proportion of broken material of <2 mm produced was 0.03% by weight.

EXAMPLE 2

The catalytic effect of the catalyst prepared in Example 1 was tested in an industrial reactor tube having an internal diameter of 20.5 mm and being externally cooled by a salt bath, with a catalyst bed depth of 2.7 m by means of the conversion of propene to acrolein.

(a) Feeds of 5 moles or propene per hour, 40 moles of air per hour and 10.1 moles of $H_2O$ per hour produced, at a salt bath temperature of 351° C., a conversion of 94%, an acrolein starting yield of 79.2 and a total selectivity for acrolein and acrylic acid of 92.5%.

(b) Feeds of 5 moles of propene per hour, 30 moles of air per hour and 29 moles of recycled exit gas per hour (composition: 7% of $O_2$, 1% of propene and 92% of inert gas, e.g. propene, nitrogen, carbon dioxide and water) produced, at a salt bath temperature of 355° C., a conversion of 94.9%, an acrolein yield of 79.5% and a selectivity for acrolein and acrylic acid of 92%.

EXAMPLE 3

2 kg of the precursor powder prepared as in Example 1 were suspended in 1.9 kg of water with the addition of 0.05 kg of glucose as binder. In a Driacoater 500, 6 kg of an aluminum silicate support having a specific surface area of less than 1 m²/g, a diameter of 4.8 mm, a macroporosity where 90% of the pores were between 70 and 500 μm, a surface roughness according to DIN 4,768/1 with a middle roughness value of 48 μm and a thermal expansion coefficient at 400° C. of $70 \times 10^{-7}$/°C. were given a thorough mixing and flowing motion by blowing in preheated air at 70° C. at a rate of 2 m³/min and by turning the drum at 12 rpm, and the suspension analogous to Example 1 was sprayed in the course of 35 minutes onto the support thus agitated in such a way that the exit air temperature sank from initially 43° C. to 38° C. After drying, the raw catalyst was activated at 575° C. in a revolving tube. The abrasion, measured in a La-Roche Friabilator, was 0.2% by weight.

EXAMPLE 4

A precursor powder was prepared according to Example 1, only with the difference that 0.4 kg of potassium nitrate was additionally added to the samarium oxide solution. The precursor powder calcined at 470° C. in a revolving tube had a thermal expansion coefficient of $80 \times 10^{-7}$/°C.

9 kg of this precursor material were suspended in 5.3 kg of water together with 0.7 kg of pentaerythritol (pore-former) and 0.8 kg of glucose (binder) and the suspension was sprayed in a Driacoater onto a 6 kg of thoroughly agitated steatite supports (as in Example 1). In this step, the inlet air supplied at 2.5 m³ per minute was preheated to 85° C. and the suspension sprayed on in the course of 95 minutes was metered at such a rate that the exit air temperature sank from initially 51° C. to 42° C. After drying, decomposition of pore-former and binder at 400° C. and activation at 550° C. in a revolving tube, the catalyst had an abrasion of 0.3% by weight in a La-Roche Friabilator.

EXAMPLE 5

A precursor powder was prepared analogously to Example 1 by successively adding with stirring a solution of 18.4 kg of ammonium molybdate $(NH_4)_6Mo_7O_{24} \cdot 4H_2O$ in 24.1 kg of 3.1% strength phosphoric acid, a solution of 7 kg of bismuth nitrate $Bi(NO_3)_3 \cdot 5H_2O$ in 7.0 kg of 0.8% strength nitric acid and 6 kg of pyrogenic silica (Aerosil®200) to a solution of 6.7 kg of nickel nitrate $Ni(NO_3)_2 \cdot 6H_2O$, 12.3 kg of cobalt nitrate $Co(NO_3)_2 \cdot 6H_2O$ and 6.9 kg of ferric nitrate $Fe(NO_3)_3 \cdot 9H_2O$ in 30.4 kg of water. The resulting coprecipitate was dried at 140° C. on a drum dryer and calcined at 535° C. in a revolving tube and then milled in a pin mill.

The resulting powder had a particle size distribution of 5–80 μm (90% value) with a maximum at 30 μm and a thermal expansion coefficient of $85 \times 10^{-7}$/°C.

An abrasion-resistant coated catalyst was prepared in a Driacoater 500 in a manner corresponding to Example 1 from 7.5 kg of this precursor powder with an addition of 0.6 kg of glucose and 0.5 kg of pentaerythritol in 6.2 kg of water and 6 kg of steatite support. The abrasion ws 0.25% by weight in a La-Roche Friabilator.

EXAMPLE 6

A precursor powder was prepared as in Example 5, but with the additional presence of 0.2 kg of $KNO_3$ in the first solution. The resulting powder had a particle size distribution of 3–70 μm (90% value) with a maximum at 25 μm and a thermal expansion coefficient of $84 \times 10^{-7}$/°C.

An abrasion-resistant coated catalyst was prepared in a Driacoater 500 in a manner corresponding to Example 1 from 5.5 kg of this precursor powder with 0.4 kg of glucose in 4.5 kg of water and 6 kg of steatite support. The abrasion was 0.3% by weight in a La-Roche Friabilator.

EXAMPLE 7

50 ml of the catalyst prepared in Example 5 were packed into a tube reactor which had an internal diameter of 16 mm and was externally temperature-controlled to 362° C. by a salt bath. Feeds, per hour, of 0.25 mole of propene, 45 liters (S.T.P.) of air and 9.5 g of water produced a conversion of 92.5%, an acrolein yield, relative to propene used, of 80.5% and a total selectivity, relative to propene used, of 95.8%.

EXAMPLE 8

50 ml of the catalyst prepared in Example 3 were packed into a reactor which had an internal diameter of 16 mm and was externally temperature-controlled to 370° C. by a salt bath. Feeds, per hour, of 0.15 mole of isobutene, 35 liters (S.T.P.) of air and 10.5 g of water produced a conversion of 91%, a methacrolein yield of 74.1%, relative to isobutene fed in, and a total yield of methacrolein and methacrylic acid of 82.4%.

EXAMPLE 9

50 ml of the catalyst prepared in Example 4 were packed into a reactor which had an internal diameter of 16 mm and was externally temperature-controlled to 355° C. by a salt bath. Feeds, per hour, of 0.15 mole of t-butanol, 35 liters (S.T.P.) of air and 10.5 g of water produced a conversion of 92.8%, a methacrolein yield of 75.2%, relative to t-butanol fed in, and a total yield of methacrolein and methacrylic acid of 81.9%.

EXAMPLE 10

50 ml of the catalyst prepared in Example 6 were tested as in Example 8 at a salt bath temperature of 382° C. The conversion was 93.6%, the methacrolein yield as 75.6%, relative to isobutene fed in, and the total selectivity for methacrolein and methacrylic acid was 82.9%.

We claim:

1. In a process for preparing acrolein from propylene wherein there is carried out an oxidation in oxygen-containing gas mixtures in the presence of an active catalyst material of the composition:
$Ni_aCo_bFe_cBi_dP_eMo_fO_x$ in which a is a number from 2–20, b is a number from 0–15, a and b are a number from 2–20, c is a number from 0.1–7, d is a number from 0.1–4, e is a number from 0.1–4, f is about 12 and x is a number from 35–85, and 0.2 to 5% by weight of tantalum or samarium, calculated as $Ta_2O_5$ or $Sm_2O_3$, and a carrier therefor, said carrier being composed of a layer lattic silicate and/or highly dispersed silica, the weight ratio silicate to silica being 10:1 to 1:1, the improvement wherein an abrasion resistant coated catalyst is employed, said coated catalyst having an inert support which has a particle size of 0.5 to 6 mm and a rough surface and a coating enclosing said support and anchored in it, which coating is obtained by spraying a suspension of the starting material for the coating onto an agitated bed of the support while the suspending medium is partially removed by a gas stream at 20°–250° C. and an essentially constant residual moisture of the coating is being maintained, and drying and heat-treating, wherein coated catalysts are used for the oxidation in the preparation of which the support bed is set into mixing motion by mechanical agitation and is simultaneously loosened by blowing in from below a fluidizing, mixing-intensifying gas stream, and a suspension of a precursor of the catalytically active material, which suspension contains a binder, is passed countercurrent to the gas in this bed at a rate which increases with increasing thickness of the coating, the amounts of suspending medium drawn off and sprayed on being maintained in a substantially constant ratio which is determined by the particular combination of support and precursor used and the thermal expansion coefficients of support and of dried pulverulent precursor being so chosen that they differ by at most 15%, and wherein after the spraying-on has been completed the coating is densified by continuing the increased mixing motion, the mechanical mixing motion is then stopped, the material is dried in a continuing gas stream and finally heat-treated.

2. In a process for preparing methacrolein from isobutylene or tertiary butanol wherein there is carried out an oxidation in oxygen-containing gas mixtures in the presence of an active catalyst material of the composition:
$Ni_aCo_bFe_cBi_dP_eMo_fO_x$ in which a is a number from 2–20, b is a number from 0–15, a and b are a number from 2–20, c is a number from 0.1–7, d is a number from 0.1–4, e is a number from 0.1–4, f is about 12 and x is a number from 35–85, and 0.2 to 5% by weight of tantalum or samarium, calculated as $Ta_2O_5$ or $Sm_2O_3$, and a carrier therefor, said carrier being composed of a layer lattice silicate and/or highly dispersed silica, the weight ratio silicate to silica being 10:1 to 1:1, the improvement wherein an abrasion resistant coated catalyst is employed, said coated catalyst having an inert support which has a particle size of 0.5 to 6 mm and a rough surface and a coating, enclosing this support and anchored in it, which coating is obtained by spraying a suspension of the starting material for the coating onto an agitated bed of the support while the suspending medium is partially removed by a gas stream at 20°–250° C. and an essentially constant residual moisture of the coating is being maintained, and drying and heat-treating, wherein coated catalysts are used for the oxidation in the preparation of which the support bed is set into mixing motion by mechanical agitation and is simultaneously loosened by blowing in from below a fluidizing, mixing-intensifying gas stream, and a suspension of a precursor of the catalytically active material, which suspension contains a binder, is passed countercurrent to the gas in this bed at a rate which increases with increasing thickness of the coating, the amounts of suspending medium drawn off and sprayed on being maintained in a substantially constant ratio which is determined by the particular combination of support and precursor used and the thermal expansion coefficients of support and of dried pulverulent precursor being so chosen that they differ by at most 15%, and wherein after the spraying-on has been completed the coating is densified by continuing the increased mixing motion, the mechanical mixing motion is then stopped, the material is dried in a continuing gas stream and finally heat-treated.

3. The process as claimed in claims 1 or 2, wherein the coated catalyst is obtained by adjusting the fluidizing gas stream to a specific flow rate of 15–50 Nm³ per hour per liter of support and using water as suspending medium.

4. The process as claimed in claims 1 or 2, wherein the coated catalyst is obtained by using a suspension which is comprised of 20 to 80% by weight of the pulverulent precursor.

5. The process as claimed in claims 1 or 2, wherein the coated catalyst is obtained by using a suspension which is 40 to 70% by weight of the pulverulent precursor.

6. The process as claimed in claims 1 or 2, wherein the coated catalyst is obtained by using a suspension which contains, as binder, 2–5% by weight of glucose of urea.

7. The process as claimed in claims 1 or 2, wherein the coated catalyst is obtained by using a suspension of the pulverulent starting material for the coating, which suspension contained 1–10% by weight, relative to the weight of this material, of a finely divided pore-former which is sparingly soluble in the suspending medium and which was removed below the heat treatment temperature by thermolysis or oxidation.

8. The process as claimed in claims 1 or 2, wherein the coated catalyst is obtained by using a precursor comprised of a coprecipitate of combined salt solutions of the catalytically active elements which has been dried or calcined below the heat treatment temperature.

9. The process as claimed in claims 1 or 2, wherein the precursor of the coated catalyst used is a powder having a particle size distribution of 1–150 μm.

10. The process as claimed in claims 1 or 2, wherein the amount of pulverulent precursor of the coated catalyst used is 0.1–2 times the support weight.

11. The process as claimed in claims 1 or 2, wherein the support of the coated catalyst used is α-alumina, aluminum silicate, magnesium silicate or silicon carbide.

12. The process as claimed in claims 1 or 2, wherein the roughness of the support surface has a middle roughness value of 5–50 μm according to DIN 4,768/1, as measured with the Hommel roughness meter.

13. The process as claimed in claims 1 or 2, wherein to prepare the coated catalyst, the thermal expansion coefficient of the precursor powder was matched to the coefficient of the support by a heat pretreatment at 250°–600° C.

14. The process as claimed in claims 1 or 2, wherein the oxygen-containing gas mixture supplied to the oxidation reaction of the coated catalyst has a molar ratio of olefin or alcohol to oxygen and diluting substantially inert constituents of 1:1.5–2.5:7–20.

15. The process as claimed in claims 1 or 2, wherein the oxygen-containing gas mixture contains, as diluting, substantially inert constituents, nitrogen, steam, carbon oxides and saturated aliphatic hydrocarbons having 1–5 C atoms or mixtures thereof.

16. The process as claimed in claims 1 or 2, wherein the oxidation of propylene to acrolein is carried out at a molar ratio of propylene:oxygen:nitrogen:steam of 1:1.5–1.8:5.5–7:2–4 and at a specific loading of 2–6 moles of propylene per kg of coated catalyst per hour.

17. The process as claimed in claims 1 or 2, wherein the oxidation of propylene to acrolein is carried out by partially or completely replacing a steam feed by an inert gas mixture at a molar ratio of propylene:air:inert gas:water of 1:7–9:3–8:0–2 and at a specific loading of 2–6 moles of propylene per kg of coated catalyst per hour.

18. The process as claimed in claims 1 or 2, wherein the inert gas used is the reaction exit gas freed of acrolein, acrylic acid and other constituents condensable within the temperature range of 0°–40° C.

19. The process as claimed in claims 1 or 2, wherein the inert gas contains 0.5–7% by volume of steam.

20. The process as claimed in claims 1 or 2, wherein the oxidation of isobutene or tertiary butanol to methacrolein is carried out at a molar ratio of isobutene or tertiary butanol:oxygen:inert gas:steam of 1:1.5–2.5:5-.5–10:2–10 and at a specific loading of 1–6 moles of starting compound per kg of coated catalyst per hour.

21. The process as claimed in claim 1, wherein 0.05 to 3.0% by weight of an alkali metal or alkaline earth metal, calculated as oxide is present in the catalyst, a pore-former is added to the suspension, and the material is heat treated at 0.05–5 hours at 520°–650° C., after decomposition of an added pore-former.

* * * * *